United States Patent [19]

Rocha De Albuquerque Lucio et al.

[11] Patent Number: 5,684,155

[45] Date of Patent: Nov. 4, 1997

[54] PROCESS FOR THE EXTRACTION AND PURIFICATION OF ALKALOIDS

[75] Inventors: Elisabeth Maria Rocha De Albuquerque Lucio; Claudio Luiz Correa Viana, both of Campinas; Francisco José Falcao De Andrade, Aguas de Sao Pedro; Marcello Burchianti, Sao Paulo, all of Brazil; Gilberto Burchianti, Leghorn, Italy

[73] Assignee: Polis A.G., Vaduz, Liechtenstein

[21] Appl. No.: 591,572

[22] PCT Filed: Jul. 6, 1993

[86] PCT No.: PCT/EP93/01737

§ 371 Date: Jan. 11, 1996

§ 102(e) Date: Jan. 11, 1996

[87] PCT Pub. No.: WO95/01984

PCT Pub. Date: Jan. 19, 1995

[51] Int. Cl.$^6$ .............................. C07G 5/00; C07D 405/06
[52] U.S. Cl. ............................................ 548/315.4; 514/397
[58] Field of Search ........................... 548/315.4; 514/397

[56] References Cited

U.S. PATENT DOCUMENTS

| | | | |
|---|---|---|---|
| 3,631,059 | 12/1971 | Gooriey et al. | 260/309 |
| 4,045,558 | 8/1977 | Smith et al. | 548/315.4 X |
| 4,076,942 | 2/1978 | Smith et al. | 548/315.4 |
| 5,025,027 | 6/1991 | Rapoport et al. | 548/315.4 X |
| 5,059,531 | 10/1991 | Reuter | 548/315.4 X |

FOREIGN PATENT DOCUMENTS 92-14693  9/1992  WIPO .................. 548/315.4

*Primary Examiner*—Floyd D. Higel
*Attorney, Agent, or Firm*—Browdy and Neimark

[57] ABSTRACT

A process for the extraction and purification of alkaloids from plant material wherein the first extraction is conducted with an aqueous solution of a strong acid and the acid extract is clarified by flocculation. The alkaloid is recovered from the clarified extract in a second extraction step by means of an organic solvent, or be absorption on a cationic exchange resin or by adsorption on an adsorbing material. The alkaloid is then recovered and purified. With respect to the known processes the extraction time is reduced as well as the isomerization cases and costs and risks involved with the use of organic solvents. Most of impurities are precipitated with the flocculation thus making easier the recovery of the alkaloid.

14 Claims, No Drawings

PROCESS FOR THE EXTRACTION AND PURIFICATION OF ALKALOIDS

DESCRIPTION

1. Field of the Invention

The present invention relates to a process for the extraction and purification of alkaloids from plant materials and tissues.

In particular, the invention relates to a process for the extraction and purification of pilocarpine from leaves of Pilocarpus Microphillus.

2. Description of the Prior Art

The presently known processes for the extraction of the alkaloids from plant materials (leaves, roots and so on) are based on the use of either polar organic solvents, such as methil alcohol, ethil alcohol, chlorinated solvents and the like, or non-polar organic solvents, such as benzene, toluene and the like, that are contacted with the starting plant material previously treated with aqueous sodium carbonate, aqueous ammonia or other alkalinizing substances suitable of converting the alkaloid from the form in which it is linked to the tissues to a free base soluble in the organic solvents.

The organic extract thus obtained contains considerable amounts of chlorophille and other natural compounds present in the plant material that greatly hinder the subsequent phases of extraction and purification of the alkaloid.

The process conditions (high pH, hot extraction, long stay of the drug in the extractor, etc.) greatly favour the isomerization of some alkaloids, such as for instance in the case of pilocarpine, a part of which in such conditions is changed into isopilocarpine, which is uneffective from the pharmacological point of view.

Furthermore, the high amount of the solvent used (more than 6 times the weight of the raw material to be extracted) requires expensive operations for the recovery of the same.

According to the known processes, the alkaloid is then extracted from the organic solvent with aqueous solutions of mineral acids, whereby it is transformed from a free base into a salt soluble in an aqueous solution of the used acid, or it is recovered as free base by complete evaporation of the solvent.

U.S. Pat. No. 3,631,059 discloses a process where the alkaloid is extracted from the plant material by using a diluted aqueous solution of a strong mineral acid or a strong organic acid, neutralizing then the acid aqueous extract to a pH between 5 and 13 and adsorbing the alkaloid on activated carbon, separating the carbon by which the alkaloid has been adsorbed from the exhausted solution and finally eluting the alkaloid with an aqueous solution of a strong mineral acid or a strong organic acid. In this type of process the aqueous extracts resulting from the extraction with diluted acid solutions contain various types of impurities coming from the plant (chlorophille and other pigments, sugars, starch, proteins, tannin, fat, etc.) which cannot be removed either by filtration or by strong centrifugation. Such impurities lead to a quick exhaustion of he carbon and also, after the alkalinization, give rise to stable emulsions which make extremely difficult the subsequent phases of the process. In the last analysis, the process according to the above mentioned U.S. patent, though providing an alternative to the use of organic solvents for the extraction of alkaloids from plant tissues, is however not workable in practice due to the above described incoveniences.

The purpose of the present invention is to provide a process for the extraction and purification of alkaloids from plant tissues and plant materials in general, which would be suitable from one side to take advantage from the extraction with aqueous acid solutions instead of with organic solvents and, from the other side, be effective and workable at industrial level.

SUMMARY OF THE INVENTION

The novel features of the process according to the invention consist in that for the clarification of the extract there is provided for the addition of coagulative agents with a consequent flocculation and sedimentation of the suspended impurities the concentration of said agents in said extract being at least 2 g/l. Moreover, the extraction of the alkaloid from the clarified extract comprises either of the following operation: (1) alkalinization of the solution and addition of a polar or non-polar organic solvent, which the alkaloid is extracted from; (2) absorbing the alkaloid on cationic exchange resin, copiously washing with water and eluting with an aqueous solution of a strong base to solubilize the alkaloid as free base to be extraxted with a polar or non-polar solvent; (3) adsorbing the alkaloid on an adsorbing material, copiously washing with water and eluting with a diluted aqueous solution of a strong mineral acid or an organic solvent or an aqueous solution of a strong mineral acid added with 5 to 20% of a water soluble organic solvent.

In this way the extraction time is greatly reduced, with respect to the conventional processes, as well as the isomerization cases and the costs and risks involved with the use of organic solvents. Furthermore, by extracting the alkaloid with an aqueous solution of strong acids at the conditions according to the process of the invention, the entrainment of chlorophille and other pigments with the extract is avoided. Finally, the clarification of the extract by flocculation results in the precipitation of most of the impurities and the alkaloid can be isolated from the clarified solution with either one of the above mentioned methods.

BEST MODE OF CARRYING OUT THE INVENTION

The process of extraction and purification of the alkaloids according to the present invention comprises a preliminary treatment of the starting plant material consisting of a size reduction thereof, for example a milling of the dried leaves or a comminuting of the only partially dried, or even fresh, leaves. This operation is not always necessary, but it is anyway advisable to reduce the time required for the extraction. Subsequently the size-reduced material is alkalinized with alkaline solutions (for example aqueous solutions of ammonium hydroxide, ammonium carbonate, sodium hydroxide, sodium carbonate, etc.), this treatment being not always necessary, but often advisable in some particular cases.

After size reduction and possible alkalinization of the plant material, the alkaloid is extracted from the latter by means of an aqueous solution of a strong mineral acid or a strong organic acid (such as, for example, diluted solutions of hydrochloric acid, sulphuric acid, nitric acid, acetic acid, etc.). It has been found that the amount of solution necessary to exhaust completely the drug is equal to about 10 times the weight of the starting plant material with a concentration comprised between 1 and 10% by weight of acid at a temperature lower than 60° C.

The extract is then filtered by means of pressure filters or vacuum filters, of the very thin type (1–10 micron). Coagulative agents (such as alluminium sulphate, calcium hydroxide, alluminium polychlorides, ferric chloride, etc.

alone or their mixtures), are then added to the filtered extract and the subsequent flocculation and sedimentation can be performed in a conventional continuous or intermittent flocculator-thickener, which, when requested by the fat content, can be equipped with a fat and foam surface collector. The clarification operations must be repeated at different pH values in some cases. In particular, coagulative agents can be added to the extract when it is in an acid phase, or, anyway, at a pH value lower than that at which they are active. The coagulation is then caused to occur by increasing the pH of the extract by addition of alkalinizing substances or alkalinizing solution up to the pH value requested for the coagulation to occur.

The clarified aqueous solution is then subjected to a second extraction to recover the alkaloid. The second extraction can be performed with an organic solvent: the solution containing the alkaloid is first alkalinized by addition of aqueous solution of ammonium hydroxide or carbonate, or sodium hydroxide or carbonate, up to a pH higher than 9, and then the organic solvent which extract the alkaloid as free base is added. As an organic solvent both polar organic solvents (such as methanol, ethanol, chlorinated solvents and the like) or non-polar organic solvents (such as benzene, toluene, and the like) can be used.

As an alternative the second extraction of the alkaloid from the clarified first extract can be carried out by preliminarly absorbing the alkaloid on ionic exchange resins: the clarified aqueous solution (with a pH between 5 and 7) is passed through a column filled with a H-form cationic exchange resin that retains the alkaloids. After a copious washing of the extraction column with demineralized water to the end of removing most of the impurities, the resin-absorbed alkaloid is eluted using an aqueous solution of a strong base with a pH between 10 and 14, (for example sodium hydroxide from 1 to 5% by weight, possibly with the addition of 1 to 10% of a water miscible organic solvent, such as methanol, ethanol, and the like); the strong base substitutes the alkaloid which passes into solution as free base.

As a further alternative process for the extraction of the alkaloid from the clarified first extract it is possible to proceed by preliminarly adsorbing the same alkaloid on macroporous polymers or other equivalent adsorbing material. The clarified aqueous solution, with a pH between 7 and 10, is passed through a column filled with macroporous polymers or other equivalent adsorbing material capable of retaining the alkaloid. Depending upon the type of adsorbing material it can be more convenient, instead of working with a column, to mix the adsorbent material directly to the liquid to be treated, under gently stirring. The proper time for the adsorption varies mainly as a function of the type of the adsorbing material. Once the adsorption has been completed, the extraction column is repeatedly washed with demineralized water, to the end of removing most of the impurities, or, in the case of a direct mixing, after separation of the absorbing material from the mother water by filtration and/or centrifugation, it is copiously washed for the same purpose. The adsorbate is then eluted according to either one of the following methods:

a) by means of an aqueous solution of a strong mineral acid (such as for example a diluted solution of hydrochloric acid, sulphuric acid, etc.);

b) by means of an organic solvent.

c) by means of aqueous solution of a strong mineral acid added with 5 to 20% of a water soluble organic solvent.

According to the type of treatment to which the material is subjected during the second extraction and according to the type of the coagulant utilized, the clarified first extract can be alkalinized to bring the pH to the requested optimum values; to that end aqueous solution of ammonium hydroxide, ammonium carbonate, sodium hydroxide, sodium carbonate and the like can be used.

The liquid coming from the second extraction, depending on the method utilized, can be either in the form of a solution of a free base in organic solvent, or as an alkaline aqueous solution of the free base in water or in a water-alcohol mixture, or finally as an acid aqueous solution of the salt of the alkaloid and the acid to be used.

In the case of a solution of the alkaloid as free base in water or water-solvent solution, the purification can be accomplished, after a possible pH correction by the addition of alkalinizing solution, by extracting the free base in an organic solvent essentially water immiscible, for example some chlorinated solvents. After the separation of the exhaust alkaline solution from the organic solvent, the latter is evaporated, preferably under vacuum, so as to maintain a temperature lower than 60° C. The concentrated solution of the free base is then treated with a solution of a strong mineral acid, so as to obtain the salt of the alkaloid. A higher purification is accomplished by dissolution and recrystallization of the salt (in methonal or methanol-acetone mixture) or by passing a salt solution on a cationic exchange resin column to absorb the alkaloid that can be then eluted again as previously described.

In the case of a solution of the free base in an organic solvent it can be proceeded directly to the concentration preferably under vacuum condition and then to the treatment with a strong mineral acid so as to obtain the salt of the alkaloid and then proceed as above.

In the case of an acid solution of the salt of the alkaloid and the acid used, the solution can be purified either directly, passing it on a column of cationic exchange resins, as described above, or alkalinizing the solution, extracting it in an organic solvent and final concentration under vacuum and acid treatment.

The selection among the different methods to accomplish the second extraction and the purification of the alkaloid depends, besides on the very nature of the alkaloid, on economical reasons, availability of the equipment and of materials, etc.

The process for the extraction and purification of the alkaloids according to the present invention, although valid as a general method for the extraction of most of alkaloids of plant origin, even in the cases where the fat content in the starting material is higher than 0.5%, has proven particularly suitable for the extraction of pilocarpine from leaves of Pilocarpus Microphillus Stapf (Maranham Jaborandi), Pilocarpus Jaborandi Holmes (Pernambuco Jaborandi) and Pilocarpus Pinnatifolius Lamaire (Paraguay Jaborandi), (Familia Rutacee). Some cases of practical working of the process according to the present invention are given here below as non limiting examples.

EXAMPLE NO. 1

100 Kg of completely dried Pilocarpus Microphillus leaves were comminuted in a hammer mill and sieved with 6 mm mesh sieve. The analysis conducted on the raw material gave a total content of alkaloids equal to 0.65%.

The plant material was extracted twice, each time with 600 l of a 2% sulphuric acid aqueous solution. The analysis of the exhausted plant material revealed only traces of total alkaloids initially present in the starting material.

The acid extract was allowed to settle overnight, then was filtered with a 10 micron filter and neutralized to pH 6.9 with a solution containing equal parts of calcium hydroxide, sodium hydroxide and ammonium hydroxide. The neutralized extract was added with 0.2% (wt/vol) of a combination of equal parts of ferric chloride and activated silica. After a proper mixing the extract was allowed to settle for five hours and then filtered with a 1 micron filter. The sludge was washed and stirred in water (six times its weight) and after decantation the supernatant liquid was separated, filtered and added to the previously separated extract. The residual sludge was disposed of.

The extract was neutralized and, then brought to a pH higher than 9 by addition of a concentrated solution of ammonium hydroxide. After a further filtration on a 1 micron filter, the liquid was fed to a static extractor where it was extracted twice with chloroform (20% vol/vol.).

The chloroformic phase was separated and completely evaporated under vacuum at a temperature lower than 50° C. The concentrated base obtained in this way was dissolved in an amount of ethanol equal to five times the weight of the base, concentrated nitric acid was then added under stirring and maintaining the temperature always below 10° C., up to reaching a titration corresponding to a pH equal to 4.

After the precipitation of the pilocarpine nitrate, the mixture was concentrated at one third of the initial volume and cooled to 0° C. for six hours. The pilocarpine nitrate, once filtered, was dissolved again in an amount of methanol equal to eight times its weight, then recrystallized to remove secondary alkaloids and other impurities. The product obtained in this way met USP XXII specification perfectly.

The mother waters contaning pilocarpine and other secondary alkaloids were evaporated under vacuum at a temperature lower than 60° C. The residue was dissolved in water (five times its weight), the solution was alkalinized to a pH higher than 9 with ammonium hydroxide and then extracted with chloroform repeating then the above described steps. The pilocarpine nitrate obtained in this way also met USP XXII specification perfectly.

The total extraction yield was 75.6%

EXAMPLE NO. 2

80 Kg of completely dried Pilocarpus Microphillus leaves were comminuted in a hammer mill and sieved with 5 mm mesh sieve. The analysis conducted on the raw material gave a total content of alkaloyds equal to 0.87%.

The plant material was extracted twice in a conventional type static extractor with 500 l of a 1.8% hydrochloric acid aqueous solution each time. The analysis of the exhausted plant material revealed only traces of total alkaloids initially present in the starting material.

The acid extract was neutralized to pH 6.5 with a solution comprising equal parts of calcium hydroxide and ammonium hydroxide and was filtered with a 5 micron filter. A 0.3% (wt/vol) of a equal parts combination of alluminum sulphate and activated silica was added to the neutralized extract in a continuous type flocculator-thickener. After the flocculation and the thickening the sludge was washed with water (ratio 1/4), centrifugated and disposed of, while the washing liquid was filtered and, after a pH correction to 6.8, filtered again and added to the already clarified extract.

The clarified extract was allowed to circulate on a column of cationic exchange resin of the strong acid type with macroporous structure in the form H, up to a complete exhaustion of the content of alkaloids that were absorbed on the resin. The column was then washed with water at pH 7 so as to remove the impurities still remaning after the previous processing. The resin was then extracted slowly with 300 l of 1% sodium hydroxide aqueous solution. The drug was then eluted in the washing alkaline solution, from which it was extracted as free basis in chlorofom phase with three chloroform washing (10% vol/vol) in a liquid extractor.

Having ascertained that the exhausted alkaline solution was substantially free of a alkaloids it was disposed of. The chloroformic phase was separated and then completely evaporated under vacuum at a temperature lower than 50° C. The concentrated base contained in this way was dissolved in a methanol-acetone solution (vol. 8 times the weight), cooled to 0° C. and hydrochloric acid up to a titration corresponding to a pH of 4 was added under stirring and maintained temperature always below 40° C.

A copious precipitate of pilocarpine hydrochloride was obtained, which was filtered and then dissolved again in methanol (vol. 8 times the weight) and recrystallized to remove any secondary alkaloids and other impurities. The pilocarpine hydrochloride met USP XXII specification perfectly.

The mother waters contaning minor parts of pilocarpine hydrochloride and other secondary alkaloids were completely evaporated under vacuum at a temperature below 50° C. The residue was dissolved in water (10 times its weight), then the solution was absorbed on a cationic resin up to a almost complete exhaustion of its alkaloid content. After having washed the column twice with 10 l of water each time, the alkaloid was extracted by elusion with a 1% sodium hydroxide solution. The alkaline solution was then extracted with chloroform.

The chloroform phase was separated and then completely evaporated at a temperature below 50° C. The concentrated base was dissolved in a methanol-acetone solution (vol. 8 times the weight), cooled to 0° C. and hydrochloric acid up to a titration corresponding to a pH of 4 was added under stirring and maintaining the temperature again below 40° C., thus obtaining a satisfactory precipitation of pilocarpine hydrochloride which was filtered and then dissolved again in methanol (vol. 8 times the weight) and recrystallized to remove any secondary alkaloids and other impurities. The pilocarpine hydrochloride obtained in this way met perfectly the USP XXII specification.

The total yield was 81.8%.

EXAMPLE NO. 3

20 Kg of completely dried Pilocarpus Microphillus leaves were milled in a hammer mill and sieved in a 4 mm mesh sieve. The analysis conducted on the raw material revealed a total alkaloids content of 0.77%.

The plant material was extracted three times with 100 l of a 4% tartaric acid aqueous solution each time using a conventional type static extractor. The analysis of the exhausted plant material revealed traces of the total alkaloids initially present in the starting material.

The acid extract was alkalinized with a equal part calcium hydroxide and amminum hydroxide solution up to pH 6.6, allowed to settle overnight and then filtered with a 50 micron filter. The neutralized extract was added with 0.8 (wt/vol) of a equal part combination of cationic polyelectrolites and sodium alluminate. After flocculation and thickening, the clarified extract was filtered with a 1 micron filter, the sludge was centrifugated and disposed of, while the sludge extraction liquid was filtered and added to the previous one.

The extract was neutralized and then brought to pH 7 by addition of an ammonium hydroxide concentrated solution.

The clarified extract was allowed to circulate on a cationic exchange resin column (strong acid type) in the form H up to exhaustion of its content of alkaloids, that were absorbed on the resin.

The column was then washed with 50 l water at pH 7 to remove any present impurities. The resin was extracted slowly with 40 l of a 1.5% sodium hydroxide aqueous solution up to exhaustion of its alkaloid content. The drug was then eluted in the washing alkaline solution that was brought to pH 6.5 by sulphuric acid addition.

Afterwards, a new flocculation-thickening was carried out by addition of 0.8% coagulants (equal parts of ferrous sulphate and sodium alluminate) to the solution. After thickening the clarified solution was filtered with 1 micron filter. The sludge was washed with 6 times its weight of water, centrifugated and disposed of, while the liquid coming from centrifugation was added to the previous one after filtration with a 1 micron filter.

The processed solution was then alkalinized up to pH higher than 9 and fed to a liquid-liquid extractor where it was twice extracted under energetic stirring with 20% (vol/vol) of chloroform; the alkaloid-free aqueous phase was disposed of.

The chloroformic phase was separated and completely evaporated at a temperature below 50° C. The concentrated base obtained in this way was dissolved in a methanol-acetone mixture equal to 8 times its weight. The solution was cooled to 0° C. and then hydrochloric acid was added up to a titration corresponding to a pH of 4 by stirring and cooling in-order that the temperature increase in the course of the reaction would not go over 45° C. The formation of a copious precipitate of pilocarpine hydrochloride was then obtained.

The salt was washed, filtered and dissolved in an amount of methanol equal to 8 times its weight. Activated carbon was then added under energetic stirring. The mixture was filtered, concentrated up to half of the starting volume and maintained at 0° C. over 6 hours, under slow stirring; in this way it was obtained the recrystallization of an abundant amount of pilocarpine hydrochloride meeting the USP XXII specification.

The mother waters containing pilocarpine and other secondary alkaloids were evaporated under vacuum at a temperature below 50° C. The residue was dissolved in water (12 times its weight) and the solution was alkalinized to a pH higher than 7 with ammonium hydroxide and then extracted again on a column of cationic exchange resin up to exhaustion of the alkaloid content. After washing of the column with 6 l of water at pH 7, elusion with 4 l of 2% ammonium hydroxide solution was carried out. The alkaline solution was then extracted in chloroform and processed as described above.

The total yield of the pilocarpine extraction, referred to the amount of pilocarpine initially present in the leaves, was 80.3%.

EXAMPLE NO. 4

10 kg of completely dried Pilocarpus Microphillus leaves were milled in a hammer mill and sieved with a 5 mm sieve and fed to a conventional type static extractor. The analysis of the raw material revealed a total alkaloid content equal to 0.87%.

The plant material was extracted with three subsequent washings each 50 l of a 3% acetic acid aqueous solution. Tests on the exhaust plant material revealed a substantially complete extraction of the initially present alkaloids.

The acid extract was treated with a solution comprising equal parts or calcium hydroxide and sodium carbonate up to pH 4.5 and allowed to settle overnight. The acid extract was then filtered with a 50 micron filter and added with a sodium carbonate solution so as to bring the pH to 6.95 and it was proceeded with a second filtration with 1 micron filter.

The neutralized extract was treated with the addition of coagulants (0.36% wt/vol of equal parts or alluminum sulphate and sodium alluminate). The clarified surnatant liquid was filtered with 1 micron filter, the sludge was centrifugated and disposed of, while the liquid extracted from the centrifuge, after filtration with 1 micron filter, was added to the previous one.

The clarified extract was alkalinized with an ammonium hydroxide solution up to pH higher than 9 and then added with coagulants (0.3% wt/vol of equal parts of ferric chloride and sodium basic silicate) and fed to a thickening tank. After the flocculation the clarified extract was filtered with 1 micron filter and the sludge was centrifugated and disposed of; the sludge extraction liquid was filtered with 1 micron filter and added to the previous one.

The clarified alkaline solution was extracted in a liquid-liquid mixer-extractor with two chloroform washings (15% vol/vol). The alkaloid free alkaline solution was disposed of. The chloroform phase was completely evaporated at a temperature below 55° C. and the free base was dissolved in ethanol (6 times its weight), concentrated nitric acid was then added, under stirring and maintaining the temperature below 10° C., up to a titration corresponding to a pH of 4. A copious precipitate of pilocarpine nitrate was thus obtained.

The mixture was concentrated to half its starting volume and cooled to 0° C. for six hours, after filtration the salt was dissolved in methanol (8 times its weight) and recrystallized as already described in the previous example to remove any secondary alkaloids and impurities. The pilocarpine nitrate obtained in this way met perfectly USP XXII specification.

The mother waters containing residual parts of pilocarpine nitrate and other secondary alkaloids, were completely evaporated at a temperature below 50° C. The residue was dissolved in water (20 times its weight), then the solution was alkalinized with ammonium hydroxide up to pH higher than 9. The alkaline solution was treated with the addition of coagulants, clarified and filtered with 1 micron filter. The sludge was disposed of. The clarified alkaline solution was extracted with two dichloromethane washing (20% vol/vol) up to exhaustion of the alkaloid content and then disposed of. The organic phase was completely evaporated and the free base obtained was dissolved in 6 times its weight of ethanol repeating the steps of salification, crystallization, and recrystallization already described. The pilocarpine nitrate thus obtained met perfectly USP, XXII specification.

The final yield was 79.8%.

EXAMPLE NO. 5

40 Kg of completely dried Pilocarpus Microphillus leaves were milled in a hammer mill and sieved with a 4 mm mesh sieves. The analysis conducted on the raw material gave a total content of alkaloids equal to 0.82%.

The plant material was extracted twice with 220 l of a 2% hydrochloric acid aqueous solution each time using a conventional type static extractor. The analysis of the exhausted plant material revealed traces of the total alkaloids initially present in the starting material.

The acid extract was alkalinized with a equal amount of ammonium hydroxide solution up to pH 6.6, allowed to settle for five hours and then filtered with a 50 micron filter. The neutralized extract was added with 0.3% (wt/vol) of a equal part combination of cationic polyelectrolites and sodium alluminate. After flocculation and thickening the clarified extract was filtered with a 10 micron filter, the sludge was centrifugated and disposed of, the sludge extraction liquid was filtered and added to the previous one.

The extract was neutralized and brought to pH 7.5 by addition of a concentrated solution of ammonium hydroxide. After a further filtration with 1 micron filter the liquid was adsorbed on a column filled with macroporous polymers (DOW - S 112) up to complete exhaustion of its alkaloid content. The column was then washed with water at PH 7, so as to remove any residual impurities from the previous treatment and then was slowly eluted with 40 l ethil acetate. The drug was thus extracted as free base in organic phase. The organic phase was completely evaporated at a temperature below 50° C. The concentrated base obtained in this way was dissolved in a mixture of methanol and acetone equal to 7 times its weight. The solution was cooled to 0° C. and hydrochloric acid was added up to a titration corresponding to a pH of 4, under stirring and cooling in order that the temperature increase in the course of reaction would not go over 45° C. The formation of a copious precipitate of pilocarpine hydrochloride was thus obtained.

The salt was washed with acetone, filtered and dissolved in an amount of methanol equal to 6 times its weight. Activated carbon was then added under stirring. The mixture was filtered, concentrated to half of initial volume and maintained to 0° C. for six hours, under slow stirring. The crystallization of a copious amount of pilocarpine hydrochloride meeting the USP XXII specification was thus obtained.

The mother waters containing pilocarpine and other secondary alkaloids were evaporated under vacuum at a temperature below 50° C. The residue was dissolved in water (5 times its weight), the solution was then alkalinized to a pH higher than 9 with ammonium hydroxide, extracted in chloroform and then the above described steps were repeated. The pilocarpine hydrochloride obtained in this way met perfectly the USP XXII specification.

The total yield of extraction of the pilocarpine referred to the amount of total alkaloids initially present in the leaves was 78.3%.

EXAMPLE NO. 6

10 Kg of Atropa Belladonna leaves were milled in a hammer mill and sieved with a 6 mm sieve. The analysis conducted on the raw material revealed a total alkaloid content of 0.43%.

The plant material was extracted two times with 60 l each time and a third time with 100 l of a 2.2% hydrochloric acid aqueous solution using a conventional type static extractor. The analysis of the exhausted plant material revealed traces of total alkaloids initially present in the starting material.

The extracts from the first and second washing were combined (extract A, as called hereinafter), alkalinized with a solution of calcium hydroxide, sodium hydroxide and sodium carbonate (equal parts) to a pH of 6.8, and then filtered with a 5 micron filter. The neutralized extract was added with 0.7% (wt/vol) of a equal part combination of alluminum sulphate and sodium alluminate. After flocculation and thickening, the clarified extract was filtered with a 1 micron filter and the sludge was centrifugated and disposed of while the centrifugation liquid was filtered and added to the previous one.

The clarified extract was alkalinized to a pH of 9.5 and filtered on a 1 micron filter. Afterwards sulphuric acid was added under stirring to a pH of 5.5 and then neutralized with ammonium hydroxide to a pH of 7. The extract treated in this way was passed through a cationic resin column, of the strong acid type in form H, up to exhaustion of its alkaloid content and was then disposed of.

The column was first washed with 40 l of water having a pH of 7 and then eluted with 20 l of a 2% ammonium hydroxide solution (pH 11.6) up to exhaustion of its alkaloid content.

In order to evaluate the validity of the different methods under study the extract of the third washing (extract B, as called hereinafter), simultaneously with the above described steps, was alkalinized with a solution of calcium hydroxide, ammonium hydroxide and sodium carbonate (equal parts), to a pH of 5.8 and then, after filtration with a 5 micron filter, was added to 0,6% (wt/vol) of a equal part combination of ferrous sulphate and sodium silicate. After flocculation and thickening the clarified extract was filtered with 1 micron filter, the sludge was centrifugated and disposed of. The centrifugation liquid was filtered and added to the previous one; by addition of ammonium hydroxide the solution was alkalinized to a pH higher than 9.

Both the extract from exchange resin column (extract A) and that from the third washing (extract B) were treated separately in two liquid-liquid extractors, with respective washing of 20% (vol/vol) ethil acetate. The alkaloid free aqueous extracts were finally disposed of.

Each organic phase from extract A and B was evaporated under vacuum at a temperature below 45° C. separately. 38.4 g of total alkaloid as free base were obtained that will be then salified and purified with the conventional methods. The total alkaloid yield of the extraction process with respect to the total alkaloid present in the starting plant material was 89.3%.

Apart from the higher solvent consumption in the case of extract B, due to the larger amount of liquid to be treated, both methods were perfectly corresponding.

EXAMPLE NO. 7

10 Kg of Kaipalis Iperkakuana roots were milled in a hammer mill and sieved with 5 mm sieve. The analysis conducted on the raw material revealed an alkaloid content of 1.27%.

The plant material was extracted two times, with 65 l the first time and with 85 l the second time of a 2.5% sulphuric acid aqueous solution using a conventional type static extractor. The analysis of the exhausted plant material revealed only traces of total alkaloids initially present in the starting material.

The extract from first washing (65 l, extract A as called hereinafter) was alkalinized with a solution comprising 30 parts of calcium hydroxide and 70 parts of sodium carbonate to a pH of 6.3, allowed to settle overnight and then filtered with a 5 micron filter. The filtered extract was added with 1.1% (wt/vol) of a equal parts combination of alluminum sulphate, sodium alluminate and ferric chloride, and the pH was corrected to 6.5 by addition of ammonium hydroxide. After flocculation, the extract was centrifugated and filtered with 1 micron filter and the sludge was disposed of. The so treated extract was absorbed on a cationic resin column, of the strong acid, type in form H, to exhaustion of its alkaloid content and was then disposed of. The column was first washed with 20 l of water with pH of 7 and then eluted with 15 l of a 1% sodium hydroxide solution (pH 13.3) up to exhaustion of its alkaloid content.

The extract of the second washing (85 l, extract B, as called hereinafter) was alkalinized with a solution of calcium hydroxide, ammonium hydroxide and sodium hydroxide in equal parts to a pH of 6 and then added with alluminum polychloride (0.8% wt/vol), sodium alluminate (0.4% wt/vol) and ferric chloride (0.3% wt/vol) as coagulants, and the pH was corrected to 6.5 by addition of ammonium hydroxide. After flocculation and thickening, the clarified extract was centrifugated and filtered with a 1 micron filter; the sludge was disposed of. Subsequently the clarified extract was alkalinized by addition of ammonium hydroxide to a pH higher than 9.

Both the extract from the exchange resin column (extract A) and that coming from the second washing (extract B) were treated separately in two liquid-liquid extractors, each with three washing using 8% chloroform (vol/vol); both alkaloid-free aqueous extract were disposed of.

Each organic phase from extracts A and B was evaporated under vacuum at a temperature below 50° C. separately; the free base so obtained was dissolved in a mixture of methanol and acetone equal to 7 times its weight and then, after cooling to 0° C., hydrochloric acid was added to a titration corresponding to a pH of 4, under stirring and cooling so as to maintain the temperature always below 40° C. A copious precipitation of emethine hydrochloride and cephiline hydrochloride was obtained.

The salts obtained in this way were then separated and purified according to conventional methods.

Apart from the higher solvent consumption in the case of extract B, due to the larger amount of liquid to be treated, both methods were completely corresponding.

The total free base yield was 81.3% with respect to the total alkaloid present in the starting material.

We claim:

1. A process for the extraction and purification of an alkaloid or alkaloids from plant tissues comprising the steps of:
   a) contacting the plant tissues, in a comminuted form, with an aqueous solution of a strong mineral or organic acid so as to accomplish a first extraction of the alkaloid or alkaloids, said first extraction being carried out at a temperature not greater than 60° C. and said strong acid aqueous solution being at a concentration between 1 and 10%
   b) clarifying the first extract;
   c) subjecting said first clarified extract to a second extraction so as to obtain a solution containing the alkaloid in the form of a free basis or salt;
   d) purifying the alkaloid in said second extract,
   characterized in that the clarification step comprises adding one or more coagulative agents to said first extract to reach a concentration of said agents of at least 2 g/l in said first extract with the consequent flocculation and thickening of the suspended impurities.

2. The process of claim 1, wherein the amount of strong acid aqueous solution used for said first extraction is equal to about 10 times the weight of the starting plant tissue and its concentration is not greater than 5%.

3. The process according to claim 1, wherein said clarified first extract is alkalinized with an alkaline aqueous solution.

4. The process according to claim 1, wherein the coagulative agents for the clarification step are selected from the group consisting of alluminium sulphate, calcium hydroxide, alluminium polychlorides, ferric chloride, polyelectrolides, activated silica and mixtures thereof.

5. The process according to claim 1, wherein the second extraction comprises the steps of alkalinizing the first clarified extract and adding a polar or non-polar organic solvent from which the alkaloid is recovered.

6. The process according to claim 1, wherein the second extraction comprises the steps of absorbing the alkaloid on a cationic exchange resin from said first clarified extract, copiously washing with water and eluting with an aqueous solution of a strong base to solubilize the alkaloids as a free base.

7. The process according to the claim 6, wherein the aqueous solution of a strong base used for the elusion of the alkaloid absorbed on the cationic exchange resin is added with 1 to 10% by weight of a water soluble organic solvent.

8. The process according to the claim 1, wherein said second extraction comprises the, steps of adsorbing the alkaloid on an adsorbing material from said first clarified extract, copiously washing with water and eluting with a diluted aqueous solution of a strong mineral acid or with an organic solvent.

9. The process according to claim 8, wherein the diluted aqueous solution of strong mineral acid is added with 5 to 20% of a water soluble organic solvent.

10. The process according to claim 1, wherein said purification of the alkaloid from said second extract in which the alkaloid is contained in the form of a free base in water or organic solvent, comprises the steps of alkalinizing, extracting with a water immiscible organic solvent, separating the solvent from the aqueous phase, evaporating the solvent and treating the concentrated base with a solution of a strong mineral acid so as to obtain the salt of the alkaloid.

11. The process according to the claim 10, wherein the salt of the alkaloid is further solubilized and recrystallized in methanol or methanol/acetone.

12. The process according to the claim 10, wherein the solution containing the salt of the alkaloid is passed through a cationic exchange resin and eluted with an aqueous solution of a strong base.

13. The process according to the claim 11, wherein said solution containing the salt of the alkaloid is passed through a column of macroporous polymers or other adsorbing material and is eluted with a strong acid solution or an organic solvent.

14. The process according to claim 1, wherein said step of purification of the alkaloid from said second extract, in which the alkaloid is contained in the form of a free base in organic solvent, comprises the step of evaporating the solvent under vacuum and solubilizing the free base in a strong mineral acid.

* * * * *